United States Patent [19]

Bilbrey

[11] Patent Number: 5,489,427
[45] Date of Patent: Feb. 6, 1996

[54] COATING MATERIAL

[76] Inventor: James M. Bilbrey, 4538 Airway Rd., Dayton, Ohio 45431

[21] Appl. No.: 203,018

[22] Filed: Feb. 28, 1994

Related U.S. Application Data

[62] Division of Ser. No. 870,791, Apr. 16, 1992, Pat. No. 5,290,547, which is a continuation of Ser. No. 606,559, Oct. 31, 1990, abandoned.

[51] Int. Cl.$^6$ ........................................... A61L 11/00
[52] U.S. Cl. ..................... 424/76.6; 119/171; 514/937; 422/5; 252/358; 427/213
[58] Field of Search ................................... 424/76.6, 401; 422/5; 119/171; 514/937; 427/213; 252/351, 358

[56] References Cited

U.S. PATENT DOCUMENTS 5,085,849  2/1992  Sampson et al. ...................... 424/76.6

FOREIGN PATENT DOCUMENTS 0217054890827  4/1987  European Pat. Off. .
0303461  2/1989  European Pat. Off. .
01921  3/1990  WIPO .

OTHER PUBLICATIONS

R. Y. Lochhead et al. (1986). Novel Cosmetic Emulsions. *Cosmetics & Toiletries*, vol. 101, pp. 125–138.

*Primary Examiner*—Raj Bawa
*Attorney, Agent, or Firm*—Donald P. Gillette

[57] ABSTRACT

The method of making a macroemulsion composition for controlling odors and including droplets of water-immiscible, odor counteracting material dispersed as the discontinuous phase of the macroemulsion in a water soluble binder, which constitutes the continuous phase of the macroemulsion. Upon deposition of the composition onto an appropriate substrate, such as pet litter, and after evaporation of the water within the binder solution, the water soluble binder solidifies on the substrate. In so doing, the solidified water soluble binder substantially encloses the droplets of the odor counteracting material. The water soluble binder easily dissolves upon contact with water in pet excreta, thereby releasing the odor counteracting material in an amount appropriate to counteract the offensive odors at the offensive area where such counteraction is needed most.

6 Claims, No Drawings

COATING MATERIAL

This is a division of application, Ser. No. 07/870,791, filed Apr. 16, 1992, now U.S. Pat. No. 5,290,547 which is a continuation of application, Ser. No. 07/606,559, filed Oct. 31, 1990, and now abandoned.

BACKGROUND OF THE INVENTION

This invention relates to an odor counteractant to be applied as a coating on a substrate to control or modify odors resulting from the use of the substrate in contact with malodorous material and moisture. The invention further relates to the method of forming and using a macroemulsion incorporating the counteractant and to a product comprising the macroemulsion. In particular, the invention relates to the control of odors associated with the use of pet litter.

In the past, attempts have been made to control the odor in particulate pet litter by spraying an odor-modifying material directly on the litter. The odor-modifying material gave off its own odor, which was more pleasing than the odor resulting from normal use of the litter by pets, but the effect of the odor-modifying material dissipated rather soon.

An improved odor-modifying material described by Colborn et al. in U.S. Pat. No. 4,407,231 was produced by encapsulating fragrance oil as an odor counteractant in microcapsules and spraying those microcapsules on the particles of litter. The microcapsules were frangible, and the typical digging or scratching action indulged in by the pet, especially a cat, using the litter broke some of the microcapsules with each use, releasing some of the fragrance to counteract the unpleasant odors resulting from pet excreta. This same frangibility resulted in a certain amount of microcapsule breakage in handling and transportation of the containers of treated litter, which was not altogether bad, because it released a small amount of the fragrance, which would be sensed by the pet owner when opening the container of litter.

However, in actual use, it is desirable to have no further odor counteractant released until the pet uses it. When that does happen, it is not only essential that some of the microcapsules be broken, but it is further desirable that the amount of odor counteractant released be generally proportional to the need, which means generally proportional to the quantity of excreta rather than to microcapsule breakage. Breakage by mechanical scratching action is proportional to the activity of the animal and not necessarily to the amount of malodorous material that needs to be counteracted.

This further requires that the odor counteractant be carried by material that is soluble in pet urine to release the counteractant, whether the pet paws the litter intensely or little or not at all. Microcapsules, as used heretofore, are not very soluble and, thus, the fragrance oils contained in them are not released in proportion to need as specifically as is desired.

OBJECTS AND SUMMARY OF THE INVENTION

It is an object of this invention to provide an odor counteractant in a form that is easily applied to a substrate and is efficiently activated by moisture and by mechanical action in use.

Another object is to provide an efficient odor counteractant that is less expensive to produce than the microcapsules containing fragrance oils.

Still another object is to produce a coating material that includes an odor counteractant and is to be used on particulate pet litter to be released for odor control in proportion to the amount of excreta from the pet.

A further object is to provide a simple method of producing an odor counteractant having the foregoing characteristics.

Further objects will be apparent, after reading the following description, to those skilled in the art.

In accordance with this invention, an odor counteractant to be applied to a substrate for the control of odors is formed of viscous fragrance, or aromatic oil material, dispersed in high concentration as a long-lasting oil-in-water emulsion in a water-based solution of a highly water-soluble substance capable of drying to a rigid form with droplets of the suspended odor counteractant remaining dispersed individually therein.

The mixture can be applied to a substrate and given time for the water to evaporate in order to produce, on the substrate, a dry coating with the oil droplets contained therein. When moisture is brought into contact with the coating, such as by the deposit of pet excreta thereon, the moisture will dissolve the water-soluble substance, thereby releasing the fragrance oil to perform the desired function of modifying or overcoming or counteracting the odors that are either in the excreta as deposited or are generated therein over time by bacterial action.

The fragrance oil can be brought to a high viscosity by the addition of a suitable oil-soluble thickening agent so that, when dispersed, it will not tend to coalesce and will form droplets of the proper size to be easily opened by mechanical fracturing of the dried material. I have found a number of suitable thickening agents that can be used to produce satisfactory results, but, at the present time, the most satisfactory one, from the point of view of the small quantity required and the low cost, is a polymer, (polyvinyl butyral), referred to hereinafter as PVB.

There are also a number of suitable, water-soluble substances that can form aqueous solutions in which fragrance oils can be satisfactorily dispersed, and which will continue to encase the oil droplets after the water has evaporated from the solution. Gum Tahla is especially suitable to form a water-based carrier solution as a continuous phase of an emulsion in which droplets of the thickened fragrance oil can be suspended. When the emulsion has been applied to a substrate and the water component of the emulsion is evaporated, Gum Tahla, with the individual fragrance oil droplets still dispersed in it, dries to a glassy-hard, but frangible state and is still very easily dissolved in moisture. The hardened Gum Tahla encases the droplets, which are directly embedded in it without any intervening shell, as a microencapsulated droplet would have.

DETAILED DESCRIPTION OF A PREFERRED EMBODIMENT

Fragrance oils of various kinds are well known for their ability to modify odors in their vicinity, either by masking the undesired odor or overriding it or counteracting it by chemical action. In order to keep fragrance oil from escaping into the air after the oil has been applied to a substrate, this invention divides the oil into fine droplets and disperses the droplets in a carrier liquid with which the oil is immiscible, thereby forming an oil-in-water emulsion. The carrier liquid, or at least one of its components, solidifies with the oil droplets embedded in it after being applied to a substrate.

The fragrance oil can later be released by dissolving the solidified material or by breaking the solidified material along surfaces of fracture that intersect droplets of fragrance oil embedded therein. This requires that the embedding material be frangible to at least some degree, as well as being soluble in water. When the suspension is applied to particulate material, such as pet litter, it is also desirable that the solidified material not be so sticky as to cause the particles to join together in a large lump.

The oil can be dispersed in the immiscible carrier liquid by agitating a mixture of the two to form an oil-in-water emulsion, after which the emulsion can be applied as a coating material to a substrate, such as particulate material forming a pet litter, by being sprayed thereon. It is desirable that the coating material contain a high percentage of solids, or, more specifically, a high percentage of material-primarily the fragrance oil—that is insoluble in the water carrier. Furthermore, for the fragrance oil droplets to be applied uniformly with other components of the emulsion, it is necessary that the emulsion not break down, as by having the oil droplets settle out or coalesce, and that the droplets not be too small. The droplets may be from $2\mu$ to $300\mu$ but are preferably on the order of about 15 to $25\mu$ in diameter. About $20\mu$ is the most desirable size in order that any fracturing of the solidified material be likely to intersect oil droplets contained therein.

These requirements can be met by causing the fragrance oil to have a relatively high viscosity, on the order of at least about 100–1000 cps., but preferably on the order of 200–500 cps. The oil, alone, may not normally have that high a viscosity but can be made more viscous by adding to it up to about 10% by weight of a thickening agent soluble in oil. There are a number of suitable thickening agents, such as polyvinyl butyral, which is referred to in this description as PVB; hydrocarbon-soluble styrene-butadiene copolymers; hydrocarbon-soluble polyisoprene; hydrocarbon-soluble polyisobutylene; hydrocarbon-soluble polybutadiene; polystyrene; poly($\alpha$-methylstyrene); ($c_{10}$–$c_{20}$) alkyl-methylmethacrylates; ($c_{10}$–$c_{20}$) alkyl-acrylates, polyvinyl pyrrolidone; and ($c_{10}$–$c_{20}$) alkyl-methacrylate, either as homopolymers or copolymers. Petrolatum can also be used as the thickening agent. However, a weight of petrolatum equal to about half of the weight of the fragrance oil, is required to obtain viscosity in the 100–500 cps range.

I have found that, overall, PVB is the most satisfactory. While as much as about 10% by weight of PVB may be dissolved in the oil, I have found that only about 4–6% by weight of PVB need be mixed with a fragrance oil to cause the resulting mixture to have a viscosity in the desired range.

The PVB thickening agent can be mixed with some fragrance oils at room temperature; other oils must be heated to about 40° C. to about 40° C. to dissolve the PVB in the fragrance oil satisfactorily. The amount of PVB required to thicken 1 Kg of a fragrance oil is typically about 44–58 g. After these ingredients have been mixed together sufficiently to dissolve the PVB in the oil, the mixture may be set aside at room temperature for any desired time until it is needed as one of the components in forming a quantity of coating material.

The other component in the coating material is an aqueous solution of a water-soluble polymer binder. The solution is used as the continuous phase of a oil-in-water emulsion in which the thickened fragrance oil is the discontinuous phase. Suitable binders include: Gum Tahla; gum arabic; dextrin; low-molecular weight polyvinyl alcohol having a molecular weight less than about 4000; low-molecular weight polyvinyl methylether-co-maleic anhydride (PVM/MA); and Gantrez-AN, which is supplied by GAF Corp.

Of these, Gum Tahla is preferred commercially at the present time due to its low cost.

While a suitable aqueous solution of a binder may consist of about 20% to about 45% Gum Tahla by weight. Preferably at least about 30% Gum Tahla should be used, and it is not really economical to exceed about 40%. I have found that a particularly satisfactory solution can be made using the ratio of 320 g. of Gum Tahla in 680 g. of water to form a 32% solution. These ingredients can be mixed at room temperature, although the temperature can be elevated to as much as about 40° C. to speed up the dissolution of the Gum Tahla. After the mixing of these materials is complete, that mixture can also be set aside for an indeterminate time (with preservative added).

The coating emulsion is formed by mixing proper quantities of the thickened fragrance oil and the aqueous solution of the binder. The ratio of non-aqueous material to water should be between 25% and 60% by weight. In the case of an emulsion to be made using oil thickened by about 6% by weight of PVB, and a 32% solution of Gum Tahla in water, a particularly satisfactory emulsion can be made by adding the thickened oil to the Gum Tahla solution in the ratio of 200 g. of the thickened oil to 1 Kg. of the Gum Tahla solution. This is preferably done at room temperature to keep the viscosity of the oil as high as possible, since that makes the resulting emulsion more stable than if the viscosity were lower. While this can be satisfactorily done with a turbine blade stirrer revolving at about 100–200 rpm and, in relatively small batches, can even be done by hand, it is not so much the speed or mode of agitation that is of concern as the size of the droplets of fragrance oil formed in the Gum Tahla solution. As previously stated, these droplets should be about $20\mu$. This can be monitored by examining samples of them under a microscope, although, with experience, that may become unnecessary. It is known that the discontinuous phase in an emulsion intended to last for a long time should not consist of particles that re-coalesce too soon.

The reason for not making the droplets too small may be more difficult to recognize. It is desired that any fracture of the solidified Gum Tahla intersect one or more of the embedded droplets, but if the droplets are too small, the fracture may bypass them, and no fragrance oil will be released. Of course, release of even very small droplets of the fragrance oil by dissolving any volume of the solidified Gum Tahla will be expected.

Forming the emulsion can also be assisted by adding a small quantity of a surfactant, including such surfactants as sodium lauryl sulphate or one of the Spans, e.g., Span 80, which can be obtained from I.C.I. Corp., to the mixture. In forming about 1 Kg of emulsion, about 0.40 g. of sodium lauryl sulphate is ample, although its use can be avoided entirely if the main ingredients are stirred promptly. The resulting emulsion will be stable for weeks or even months. If it breaks down, it may be easily reemulsified to the proper droplet size by being stirred.

Gum Tahla, or other binder materials, will be attacked by bacteria unless such attack is prevented. To do so, I add between about 0.1% and 5% by weight of a suitable bactericide, such as Dowacil75, to the mixture as a preservative. Other suitable bactericides may also be used, such as Kathon supplied by Rohm and Haas, and Germaben supplied by Sutten Labs. The Dowacil75 can be added while the emulsion is being formed. The preferred amount of Dowacil75 in the mixture is about 1.7 g. per Kg, which is sufficient to protect the Gum Tahla from bacterial effect that would cause the emulsion to develop an unpleasant odor in a relatively short time.

The bactericide has an additional effect; it will be available to attack any bacteria brought in by the moisture when the coating is activated by that means. Thus, unpleasant odors directly emanating from the pet excreta or other malodorous material that comes into contact with the coating of this invention will be made less odious or completely eliminated by the fragrance oil, and any odors that would arise due to bacterial action, either before or after use of the coating material, will also be held in check. As a result, the material can be described as triple-acting: it provides a pleasant odor of its own; it acts as a malodor counteractant; and its bactericidal component protects the mixture before use and after use.

A small quantity of dye, typically from 0 to about 2% by weight, and preferably about 0.8% may also be added to the ingredients of the emulsion while they are being stirred together.

The formula for the ingredients of the macroemulsion are:

| | FORMULA | |
|---|---|---|
| | Preferred Value | Range of Values |
| water | 52.2% | 40–75% |
| binder | 27.3% | 15–40% |
| oil | 16.0% | 4–25% |
| preservative | 2.2% | 0.1–5% |
| dye | 0.8% | 0–2% |
| surfactant | 0.8% | 0–2% |
| thickener | 0.7% | 0–10% |

The mixture, when sprayed on pet litter, dries to a hard, glassy solid. While it dissolves readily in pet urine, it is not adversely affected by humidity nor by high ambient temperature. It can be broken up by the mechanical action of a pet's scratching the litter, and that will release at least some of the 20μ droplets of oil.

It is important that the thickness of the layer of binder, when dry, be greater than the diameter of the majority of the droplets so as to cover them. Otherwise, the droplets would not be embedded in the binder and would be exposed to the atmosphere, which would allow them to evaporate before being used to counteract an odor.

The resulting litter material is vastly superior to the prior microencapsulated material described in U.S. Pat. No. 4,407,231 because the present material dissolves so much more easily. As a result, the amount of macroemulsion required is only about half the amount of the microencapsulated material.

What is claimed is:

1. The method of making an odor-counteracting macroemulsion, said method consists essentially of the steps of:

(a) mixing a first quantity of an aqueous solution of a water-soluble polymeric binder, the binder having a weight between 15% wt. to 45% wt. of the macroemulsion and the water having a weight between 40–75% wt. of the macroemulsion, with a second quantity of odor counteractant fragrance oil having a viscosity in a range of 100–1000 cps, the odor counteractant being immiscible with the aqueous solution, to form discrete droplets of the odor counteractant in the aqueous solution without an intervening shell;

(b) optionally incorporating a surfactant; and (c) measuring the diameters of the droplets to determine that they range from 2μ to 300μ.

2. The method of making an odor-counteracting macroemulsion according to claim 1 comprising measuring the diameters of samples of the droplets microscopically to see that they do not exceed an average of about 20μ.

3. The method of making an odor-counteracting macroemulsion according to claim 1 comprising forming the odor counteractant by dissolving a thickening agent in a quantity of fragrance oil in an amount effective to increase the viscosity of the fragrance oil to a range of 100–1000 cps.

4. The method of making,an odor-counteracting macroemulsion according to claim 1 comprising forming the aqueous solution by dissolving Gum Tahla in water to form a solution in which the Gum Tahla constitutes between about 15% and 45% of the weight thereof.

5. The method of making an odor-counteracting macroemulsion according to claim 4 by dissolving an effective quantity of a water-soluble bactericide in the aqueous solution.

6. The method of making an odor-counteracting macroemulsion according to claim 1 comprising spraying the aqueous solution with the discrete droplets therein on a substrate and allowing the water in the sprayed material to evaporate.

* * * * *